US005935609A

United States Patent [19]

Denkewicz, Jr. et al.

[11] Patent Number: 5,935,609
[45] Date of Patent: Aug. 10, 1999

[54] SELF-REGULATING WATER PURIFICATION COMPOSITION

[75] Inventors: Raymond P. Denkewicz, Jr., Warwick; John D. Rafter, Providence; Mark A. Bollinger, Warwick, all of R.I.

[73] Assignee: Fountainhead Technologies, Smithfield, R.I.

[21] Appl. No.: 09/028,599

[22] Filed: Feb. 24, 1998

Related U.S. Application Data

[62] Division of application No. 08/628,405, Apr. 5, 1996, Pat. No. 5,772,896.

[51] Int. Cl.⁶ .................................................. A01N 59/16
[52] U.S. Cl. .............................................................. 424/618
[58] Field of Search .................................. 210/748, 764, 210/749; 424/618

[56] References Cited

U.S. PATENT DOCUMENTS

| | | |
|---|---|---|
| 4,173,549 | 11/1979 | Fein et al. ................................ 252/463 |
| 4,954,263 | 9/1990 | Woodhouse ............................... 210/695 |
| 5,149,354 | 9/1992 | Delaney ....................................... 71/67 |
| 5,183,496 | 2/1993 | Blenk et al. ............................... 75/702 |
| 5,192,452 | 3/1993 | Mitsui et al. ............................ 210/760 |
| 5,258,108 | 11/1993 | Cassidy .................................... 204/150 |

FOREIGN PATENT DOCUMENTS

| | | |
|---|---|---|
| 07118114 | 5/1995 | Japan . |
| 07158299 | 6/1995 | Japan . |
| 07303809 | 11/1995 | Japan . |

Primary Examiner—Jose' G. Dees
Assistant Examiner—Alton Pryor
Attorney, Agent, or Firm—Dean W. Russell; Bruce D. Gray; Kilpatrick Stockton LLP

[57] ABSTRACT

The invention relates to a water purification composition including silver metal and a second metal. The second metal is relatively reducing and helps control the overall silver cation concentration in solution. The composition effectively disinfects and removes toxic metal ions from water.

25 Claims, No Drawings

SELF-REGULATING WATER PURIFICATION COMPOSITION

This application is a divisional of U.S. Ser. No. 08/628,405 filed Apr. 5, 1996 by Raymond P. Denkewicz, Jr., John D. Rafter and Mark A. Bollinger entitled "Self-Regulating Water Purificaiton Composition," now U.S. Pat. No. 5,772,896.

BACKGROUND OF THE INVENTION

The invention relates to water purification.

In many situations, water is purified to remove microorganisms, such as bacteria or algae, and harmful metal ions, such as mercury, lead and copper. Water purification may be accomplished by filtration, providing water suitable for consumption or for use in recirculating systems such as swimming pools, hot tubs, spas and cooling towers. Water purification may also be accomplished by adding chemicals like chlorine, bromine, or silver ions to the water.

SUMMARY OF THE INVENTION

The present invention features a self-regulating water purification composition which imparts and maintains trace amounts of silver ions in water, effectively disinfecting the water while reducing the concentration of other undesirable metal ions in the water.

There are a number of aspects to the invention.

In one aspect, the invention features a water purification composition including silver metal and a second metal (e.g., zinc), where the second metal has a reduction potential with respect to a standard hydrogen electrode ($E_h$) of less than 0.34 V. The purification material is exposed to water when it flows through or exchanges into and out of a device containing the composition The water purification composition is a silver-containing material.

In another aspect, the invention features a water purification composition containing silver metal and a second metal which maintains a silver ion concentration in water between 0.01 and 0.1 ppm when water contacts the purification composition by flowing through or exchanging into and out of a device containing the purification composition.

In another aspect, the invention features a method of purifying water by removing metal ions and killing bacteria by exposing the water to a silver-containing material and maintaining a silver ion concentration in said water of between 0.01 and 0.1 ppm. The silver-containing material also includes a second metal which has an $E_h$ less than 0.34 V.

In preferred embodiments, the purification composition also contains a support material such as an inorganic oxide (e.g., alumina) which has a zeta potential, or surface charge, which is less than or equal to +20 mV at the pH of the water being treated. In other preferred embodiments, the inorganic oxide has a point of zero charge (i.e., a zeta potential of zero) of between approximately 4 and 9. The preferred inorganic oxide is alumina, most preferably basic alumina.

The water to be purified, for example, can be recirculated as in a swimming pool, spa, hot tub, or cooling tower, or may be drinking water. Oxidizing agents, such as ozone, potassium peroxymonosulfate, or free available chlorine, may be dissolved in the water.

The water purification composition may provide one or more of the following advantages. Since the silver ion concentration in the body of water is controlled by equilibrium reactions, the effectiveness of the composition is not dependent on flow rate. Therefore, there is no need to add filler material to inhibit particle erosion at high flow rates, and a device containing the purification composition can be used directly in high flow conditions such as spa filter cores without requiring modification of the plumbing system to control flow rates through the device.

When the second metal is zinc, the purification composition releases and maintains a residual concentration of zinc ions which enhances disinfection and provides algaestatic properties. Furthermore, zinc helps remove hazardous metal ions (e.g., mercury, lead) and metal ions which are known to stain pool and spa surfaces (e.g., iron, copper, manganese) effectively. The inorganic oxide, which has a slightly positive, zero, or negative surface charge, also assists in the adsorption of hazardous metal ions.

The water purification composition does not significantly alter the pH, calcium hardness, or free available chlorine in the water. The purification composition can be used in swimming pools and spas where elevated pH reduces the effectiveness of chlorine, calcium hardness must be maintained to prevent corrosion, and chlorine residuals must be maintained for disinfection.

The term "zeta potential," as used herein, means surface charge. The zeta potential of the inorganic oxide can be determined, for example, by electrophoretic mobility.

The phrase "point of zero charge," as used herein, means the pH at which the surface charge of the inorganic oxide (i.e., zeta potential) is zero.

The term "$E_h$," as used herein, means the reduction potential with respect to the standard hydrogen electrode.

The term "recirculated," as used herein, means continuous flow of the water to expose the water to the water purification device, for example, in cooling towers, spas, swimming pools, and hot tubs.

Other advantages and features of the invention will be apparent from the description of the preferred embodiment, and from the claims.

DESCRIPTION OF THE PREFERRED EMBODIMENT

The preferred water purification composition includes silver metal, an inorganic oxide having a point of zero charge between 4 and 9, and a second metal with an $E_h$ less than 0.34 V, such as zinc. The purification composition purifies water upon exposure to the water as it flows through a device containing the purification composition. Alternatively, the water can exchange into and out of a device containing the purification composition. The inorganic oxide has a zeta potential of less than +20 mV at the pH of the water being purified.

Examples of inorganic oxides having a point of zero charge between 4 and 9 include alumina, zeolites, silica, and titania. Alumina is more preferred. The preferred alumina is basic (i.e. has a zeta potential less than zero) and has a surface area of at least 0.5 $m^2/g$, and more preferably between 50 $m^2/g$ and 300 $m^2/g$. Alternatively, the inorganic oxide has a zeta potential of less than +20 mV at the pH of the water being purified.

The silver is chemically deposited on the surface of the alumina support medium by known methods. For example, the silver can be deposited by the methods described in U.S. Pat. No. 5,352,369, which is incorporated herein by reference. In addition to classical impregnation techniques, silver can be deposited onto the support medium via chemical vapor deposition, ion exchange, electroplating methods, or coprecipitation. The preferred silver content of the purification composition is between 0.1 and 10 weight percent, and more preferably between 0.5 and 3 weight percent.

Once deposited on the alumina, the silver is reduced to its elemental state, for example, by heating the alumina containing the deposited silver in a reducing atmosphere (e.g., $N_2$, $H_2$, or mixtures thereof) to a temperature between approximately 300° C. and 1050° C. Alternatively, the silver is exposed to solutions containing chemical reducing agents, e.g., dextrose, glucose, sucrose, fructose, or hydrazine, to reduce the silver to the metallic state. Exposure to ultraviolet light or microwave radiation can also be used to reduce the silver.

The second metal component of the purification composition has an $E_h$ less than 0.34 V. The second metal 10 may be in the form of a powder, shavings, turnings or larger pieces. Alternatively, the second metal may be incorporated on the inorganic oxide with the silver. It is preferred that the second metal be mixed thoroughly with the silver coated alumina. Preferred second metals include zinc, copper, aluminum, iron, or manganese. More preferably, the second metal is zinc. The second metal preferably comprises between 2 and 95 weight percent of said silver-containing material.

Purification materials containing between 5 and 98 percent by weight, and more preferably between 50 and 90 percent by weight, of silver-coated alumina are preferred.

In use, the water purification composition preferably establishes an equilibrium silver ion concentration in the range of 0.01 to 0.1 ppm, and more preferably in the range of 0.01 and 0.05 ppm, in the water that is exposed to the purification composition. The silver ions kill bacteria living in the water. It is preferred that the purification material be used in the presence of oxidizing agents dissolved in the water, such as, for example, ozone, potassium peroxymonosulfate, or chlorine.

The equilibrium silver ion concentration in the water is maintained by equilibrium reactions between: (1) the silver metal and oxidizing agents dissolved in the water; (2) silver ions dissolved in the water and the second metal; and (3) silver ions dissolved in the water and the inorganic oxide support medium. The second metal plays a key role in maintaining the equilibrium silver ion concentration in the water. When the second metal has an $E_h$ less than 0.34 V, the silver ion concentration is maintained below 0.1 ppm, according to the Nernst equation (equation 1):

$$\mathscr{E} = \mathscr{E}^0 - \frac{RT}{nF}\ln Q \qquad \text{(equation 1)}$$

where R is the gas constant (8.314 J/(K mol)), T is temperature (K), n is the number of electrons, F is the faraday constant (9.648×10⁴ C/mol), Q is the reaction quotient, $\mathscr{E}^0$ is the standard cell electromotive force (emf), and $\mathscr{E}$ is the cell emf. Fundamentally, the key half-reaction is:

$$Ag^+ + 1e^- \to Ag^0 \quad E_h = \mathscr{E}^0 = 0.80 \ V$$

Therefore, $$Q = \frac{1}{[Ag^+]}$$

According to equation 1, in order to maintain a silver ion concentration ([Ag⁺]) of approximately 0.01 ppm at room temperature, $\mathscr{E}$ is about 0.38 V. This means that a reductant with $E_h$ of around 0.38 V will maintain an equilibrium concentration of silver ions in water of around 0.01 ppm. The actual situation is affected somewhat by the other equilibria (e.g., silver metal with oxidizing agents), although the general principles apply.

Furthermore, the charged surface of the inorganic oxide can help maintain the silver ion concentration in the water and in removing hazardous metal ions. The water purification composition effectively removes metal ions, such as mercury, lead, cadmium, iron, manganese, copper, nickel, chromium, barium, and arsenate. When the second metal is zinc, zinc ions are released into the water which enhance disinfection of the water and provide algaestatic properties. The water purification device does not significantly effect pH, calcium hardness, or free available chlorine in the water.

Since the silver ion concentration in the water is controlled by equilibrium reactions, this method of water purification is essentially flow rate independent. Generally, flow rates through a device containing the water purification composition preferably are between 0.01 and 3 gallons per minute per gram of purification composition. As an alternative to flowing, the water may exchange into and out of a device containing the purification composition.

The water can recirculate through a water purification device that contains the water purification composition. For example, the water purification device may be used to treat high flow rate recirculating water systems such as spas, hot tubs, swimming pools and cooling towers. The device is also suitable for purifying drinking water. It is preferred to locate the water purification composition so that it receives filtered water. For example, the water purification composition can be located in the core of a filter.

The following Examples describe the preparation of the purification material.

EXAMPLE 1

A new, 350 gallon spa was filled with balanced tap water (pH=8.36, total alkalinity=80 mg/L, calcium hardness=100 mg/L as $CaCO_3$, temperature=40° C., [Ag⁺]<0.01 mg/L, [Zn²⁺]<0.01 mg/L, [Cl⁻]=60 mg/L). A cartridge containing 50 g of 2 wt % Ag/Al₂O₃ and 50 g Zn shot (2–14 mesh) was placed into the core of the spa filter. The cartridge was exposed to flow rates which ranged from 0 to 2 gallons per minute per gram of purification material. After 6 days of operation at 1–3 mg/L monopersulfate in chlorine equivalent units, the following parameters were recorded: pH=8.04, total alkalinity=80 mg/L, calcium hardness=100 mg/L as $CaCO_3$, [Ag⁺]=0.043 mg/L, [Zn²⁺]=0.03 mg/L. The system maintains low concentrations of Ag⁺ and Zn²⁺ ions in the water while not significantly affecting the total alkalinity, calcium hardness, or pH of the water.

EXAMPLE 2

A 350 gallon spa containing a cartridge with 50 g of 2 wt % Ag/Al₂O₃ and 50 g of Zn shot (2–14 mesh) inside the core of the filter and operating with balanced tap water (pH=8.01, total alkalinity=100 mg/L, calcium hardness=100 mg/L as $CaCO_3$, temperature=40° C., [Ag⁺]=0.08 mg/L, [Zn²⁺]=0.16 mg/L) was subjected to bather activity. Flow rates through the system ranged from 0 to 2 gallons per minute per gram of purification material. Five days each week, the spa was subjected to two bathers for a period of 20 minutes. Samples were analyzed for heterotrophic plate counts immediately before and 30 minutes after each bathing period. The monopersulfate level in chlorine equivalent units was approximately 1 ppm at the beginning of each bathing period. The detected bacteria levels are listed in Table I, where CFU denotes colony forming units.

TABLE I

| Day | CFU/mL Before Bathing | CFU/mL After Bathing |
|---|---|---|
| 1 | <1 | <1 |
| 2 | <1 | <1 |
| 3 | <1 | <1 |
| 4 | <1 | <1 |
| 7 | <1 | <1 |
| 8 | <1 | <1 |
| 9 | <1 | <1 |
| 10 | <1 | <1 |
| 11 | <1 | <1 |

EXAMPLE 3

A 350 gallon spa containing a cartridge with 50 g of 2 wt % $Ag/Al_2O_3$ and 50 g of Zn shot (2–14 mesh) inside the core of a spa filter was operated for 2 months with spa use (5 bather-hours/week). Flow rates through the system varied from 0 to 2 gallons per minute per gram of purification material. After this time, silver and zinc ion levels were measured to be 0.04 mg/L and 0.05 mg/L, respectively. Heterotrophic plate counts taken before and after bathing periods over four consecutive days all showed less than 2 CFU/mL. Monopersulfate levels were maintained at approximately 6 ppm (in chlorine equivalent units) during bathing periods when the samples were collected.

EXAMPLE 4

A 350 gallon spa containing a cartridge with 50 g of 2 wt % $Ag/Al_2O_3$ and 50 g Zn shot (2–14 mesh) inside the core of the filter was operated with balanced tap water (pH=7.93, total alkalinity=80 mg/L, calcium hardness=210 mg/L as $CaCO_3$, $[Ag^+]$=0.015 mg/L, $[Zn^{2+}]$=0.07 mg/L, $[Cl^-]$=180 mg/L) and with 20 hours/day of ozonation. Flow rates through the system varied from 0 to 2 gallons per minute per gram of purification material. Over a three week period, samples were collected for heterotrophic plate counts immediately before and 30 minutes after bathing activity. The bather demand corresponded to 7 bather-hours/week and monopersulfate levels (measured in chlorine equivalent units) ranged from 0 to 6 mg/L, with 3 to 5 mg/L being typical at the beginning of the bathing periods. The bacterial counts are summarized in Table II.

TABLE II

| Day | CFU/mL Before Bathing | CFU/mL After Bathing |
|---|---|---|
| 1 | 5 | 2 |
| 2 | <1 | <1 |
| 6 | >20 | 17 |
| 7 | 5 | 6 |
| 8 | <1 | <1 |
| 9 | <1 | no sample taken |
| 12 | <1 | <1 |
| 13 | 3 | <1 |
| 14 | <1 | no sample taken |
| 15 | <1 | <1 |
| 16 | 2 | no sample taken |
| 19 | 3 | 2 |

EXAMPLE 5

$CaCl_2$ and $NaHCO_3$ were added to three separate 1 L flasks of distilled water to balance the water. A composition of 2.5 g of 2 wt % $Ag/Al_2O_3$ and 2.5 g of Zn shot (formulated as 0.125" thick×0.25" diameter discs) were added to two of the flasks and allowed to sit for 48 hours. Nothing was added to a third flask of water which served as a control. The effect of the system on alkalinity and calcium hardness of the water is shown in Table III.

TABLE III

| Flask | Initial Alkalinity (mg/L) | Final Alkalinity (mg/L) | Initial Calcium Hardness (mg/L) | Final Calcium Hardness (mg/L) | Initial $[Ag^+]$ (mg/L) | Final $[Ag^+]$ (mg/L) |
|---|---|---|---|---|---|---|
| 1 | 140 | 140 | 150 | 150 | <0.01 | 0.019 |
| 2 | 150 | 135 | 160 | 150 | <0.01 | 0.015 |
| 3 (control) | 140 | 140 | 160 | 160 | <0.01 | <0.01 |

EXAMPLE 6

Nine metals were tested for reduction by the system which consisted of 20 g of 2 wt % $Ag/Al_2O_3$ and 20 g of Zn shot (2–14 mesh) in 500 mL of distilled water. Initial and final concentrations of metal ions were determined by atomic absorption spectroscopy. Table IV shows the metals tested and the reduction in concentration after three days.

TABLE IV

| Metal Ion | Initial Concentration (mg/L) | Final Concentration (mg/L) | Percent Reduction |
|---|---|---|---|
| Arsenic | 0.6 | 0.09 | 85 |
| Cadmium | 0.7 | 0.16 | 77 |
| Chromium | 0.6 | <0.05 | >92 |
| Copper | 0.6 | 0.05 | 92 |
| Iron | 0.9 | <0.1 | >89 |
| Lead | 1.0 | <0.05 | >95 |
| Manganese | 0.7 | <0.3 | >57 |
| Mercury | 1.2 | 0.29 | 76 |
| Nickel | 0.8 | <0.4 | >55 |

EXAMPLE 7

A 350 gallon spa contained a cartridge with 50 g of 2 wt % $Ag/Al_2O_3$ and 50 g of Zn shot (2–14 mesh) inside the core of the filter. The spa contained balanced tap water with pH=7.4, total alkalinity=50 mg/L, calcium hardness=110 mg/L as $CaCO_3$, temperature=40° C., $[Ag^+]$=0.08 mg/L, $[Zn^{2+}]$=0.18 mg/L. The system in the presence of 2.0 ppm monopersulfate (in chlorine equivalent units) was tested for its disinfection efficacy against *E. coli* (ATCC 14948). The flow rate through the system was 2 gallons per minute per gram of purification material for the first minute and 1 gallon per minute per gram of purification material thereafter. The inoculum was prepared by growing cells in Lauria Broth for 24 hours at 37° C. Inoculum was added to the spa at a concentration of approximately $6.3 \times 10^5$ CFU/100 mL. Samples were taken 0.5, 1.0, 1.5, 2.0, 2.5, 3.0, and 5.0 minutes after inoculation and immediately neutralized with 0.2 mL Deox (Taylor technologies R-0867) and 1.0 mL of a 10% sodium thioglycolate/14.6% sodium thiosulfate solution. Samples were analyzed to determine the number of remaining viable cells (shown in Table V) using serial dilutions and the spread plate method on Tryptic Soy agar and the membrane filtration method (Standard Methods, 9215D).

TABLE V

| Time (min) | Log CFU remaining/100 mL |
|---|---|
| 0.0 | 5.80 |
| 0.5 | 5.18 |
| 1.0 | 5.03 |
| 1.5 | 4.57 |
| 2.0 | 4.26 |
| 2.5 | 3.41 |
| 3.0 | 2.82 |
| 5.0 | 1.49 |

EXAMPLE 8

A cartridge containing 50 g of 2 wt % $Ag/Al_2O_3$ and 50 g of Zn shot (2–14 mesh) was tested by Herbert V. Shuster Laboratories (Quincy, Mass.) using the ANSI/NSF 50-1992 disinfection protocol. The ANSI/NSF 50 standard covers circulating system components, treatment devices, and related materials for use with swimming pools, spas, or hot tubs. The test used 58 gallons of Quincy, Mass. tap water balanced to 100 mg/L alkalinity, 140 mg/L calcium hardness as $CaCO_3$, pH=7.4, 37° C. The water contained $[Ag^+]$=0.03 mg/L. The challenge materials were 4.18 g Lander's baby oil, 1.77 g urea, $2 \times 10^6$ CFU/mL *P. aeruginosa,* and $2.2 \times 10^6$ CFU/mL *E. faecium.* Chlorine bleach was delivered to the drum following the ANSI/NSF protocol where residual chlorine levels were 0.3 mg/L after 10 minutes and 0.2 mg/L after 15 minutes. Within two minutes, *E. faecium* and *P. aeruginosa* were reduced to less than one organism/mL. The media-containing cartridge in conjunction with 0.2–0.3 mg/L chlorine was effective in disinfection of the test water within the acceptance criteria of ANSI/NSF 50-1992.

EXAMPLE 9

A test of the performance of the system in 1s conjunction with non-halogen oxidizers was performed by Herbert V. Shuster Laboratories (Quincy, Mass.) where the ANSI/NSF 50-1992 protocol was modified such that non-halogen oxidizers were added prior to the test in lieu of chlorine. Three 3000 mL samples of Quincy, Mass. tap water were balanced to 100 mg/L alkalinity, 140 mg/L calcium hardness as $CaCO_3$, and pH=7.4. The water contained $[Ag^+]$=0.06 mg/L. Three oxidizer solutions were tested: monopersulfate alone, hydrogen peroxide alone, and a combination of monopersulfate and hydrogen peroxide. The solutions with monopersulfate were prepared from potassium peroxymonosulfate and contained 3.8 mg/L monopersulfate (in chlorine equivalent units) and the solutions with hydrogen peroxide were prepared from 27% hydrogen peroxide and contained 30 mg/L $H_2O_2$. The solutions were challenged with 27 mg Lander's baby oil, 30 mg urea, $1 \times 10^6$ CFU/mL *P. aeruginosa,* and $1 \times 10^6$ CFU/mL *E. faecium.* The data show that the media-containing cartridge in conjunction with either (1) 3.8 mg/L monopersulfate, (2) 30 mg/L $H_2O_2$ or (3) 3.8 mg/L monopersulfate+30 mg/L $H_2O_2$ exceeded the 3 logarithmic unit reduction of *P. aeruginosa* and the 6 logarithmic unit reduction of *E. faecium* required by ANSI/NSF 50-1992.

Other embodiments are within the claims. For example, the silver may be added a powder, shavings or turnings, rather than being chemically deposited on the support medium. Further, the support material of the water purification composition can include other ceramic or ceramic foam materials, such as silicon carbide foams.

What is claimed is:

1. A water purification composition comprising silver metal, and a second metal, wherein said second metal is selected from the group consisting of zinc metal, magnesium metal, aluminum metal, iron metal, and manganese metal.

2. The water purification composition of claim 1, wherein said second metal is zinc.

3. A water purification composition comprising silver metal, a second metal selected from the group consisting of zinc metal, magnesium metal, aluminum metal, iron metal, and manganese metal and an inorganic oxide having a point of zero charge between 4 and 9.

4. The water purification composition of claim 3, wherein said inorganic oxide has a zeta potential less than or equal to +20 mV in water having a pH of 7.0.

5. The water purification composition of claim 3, wherein said inorganic oxide has a zeta potential less than or equal to +20 mV in water having a pH of 6.0.

6. The water purification composition of claim 3, wherein said inorganic oxide has a zeta potential less than or equal to +20 mV in water having a pH of 8.0.

7. The water purification composition of claim 3, wherein said inorganic oxide has a zeta potential less than or equal to +20 mV in water having a pH of 5.0.

8. The water purification composition of claim 3, wherein said inorganic oxide has a zeta potential less than or equal to +20 mV in water having a pH of 9.0.

9. The water purification composition of claim 3, wherein said inorganic oxide has a zeta potential less than or equal to +20 mV in water having a pH of 10.0.

10. The water purification composition of claim 3, wherein said inorganic oxide comprises alumina.

11. The water purification composition of claim 3, wherein said silver metal comprises between 0.1 and 10 weight percent of said purification composition.

12. The water purification composition of claim 3, wherein said second metal is between 2 and 95 weight percent of said purification composition.

13. A water purification composition comprising silver metal and a second metal, wherein said purification composition maintains a silver ion concentration in water between 0.01 and 0.1 ppm when exposed to said water.

14. The water purification composition of claim 13, wherein said second metal is selected from the group consisting of zinc, magnesium, aluminum, iron, or manganese.

15. The water purification composition of claim 13, wherein said second metal is zinc.

16. A water purification composition comprising silver metal, a second metal, and an inorganic oxide having a point of zero charge between 4 and 9, wherein said purification composition maintains a silver ion concentration in water between 0.01 and 0.1 ppm when exposed to said water, with the proviso that the second metal is not copper metal.

17. The water purification composition of claim 16, wherein said inorganic oxide has a zeta potential less than or equal to +20 mV in water having a pH of 7.0.

18. The water purification composition of claim 16, wherein said inorganic oxide has a zeta potential less than or equal to +20 mV in water having a pH of 6.0.

19. The water purification composition of claim 16, wherein said inorganic oxide has a zeta potential less than or equal to +20 mV in water having a pH of 8.0.

20. The water purification composition of claim 16, wherein said inorganic oxide has a zeta potential less than or equal to +20 mV in water having a pH of 5.0.

21. The water purification composition of claim 16, wherein said inorganic oxide has a zeta potential less than or equal to +20 mV in water having a pH of 9.0.

22. The water purification composition of claim 16, wherein said inorganic oxide has a zeta potential less than or equal to +20 mV in water having a pH of 10.0.

23. The water purification composition of claim 16, wherein said inorganic oxide comprises alumina.

24. The water purification composition of claim 16, wherein said silver metal is between 0.1 and 10 weight percent of said purification composition.

25. The water purification composition of claim 16, wherein said second metal is between 2 and 95 weight percent of said purification composition.

* * * * *